United States Patent [19]

Zabransky et al.

[11] 4,008,291

[45] Feb. 15, 1977

[54] SIMULATED MOVING BED ALKYLATION PROCESS

[75] Inventors: Robert F. Zabransky, Oak Brook; Robert F. Anderson, La Grange Park, both of Ill.

[73] Assignee: Universal Oil Products Company, Des Plaines, Ill.

[22] Filed: June 16, 1975

[21] Appl. No.: 587,470

[52] U.S. Cl. .......................... 260/683.43; 208/146; 252/414; 260/671 R; 260/671 C

[51] Int. Cl.² .......................................... C07C 3/52

[58] Field of Search ................. 260/671 R, 683.43; 208/146

[56] References Cited

UNITED STATES PATENTS 2,635,988  4/1953  Crowley ........................ 208/146
3,851,004  11/1974  Yang ............................. 260/671

*Primary Examiner*—Delbert E. Gantz
*Assistant Examiner*—C. E. Spresser
*Attorney, Agent, or Firm*—James R. Hoatson, Jr.; Thomas K. McBride; William H. Page, II

[57] ABSTRACT

A continuous catalytic alkylation reaction and catalyst reactivation process is carried out using a simulated moving catalyst bed to effect simultaneously in different zones of a multi-zone, fixed catalyst bed, an alkylation reaction and a reactivation of catalyst. The catalyst of the present invention is a crystalline aluminosilicate zeolite composited with a Group VIII metal hydrogenation agent, and the reactivation medium utilized includes alkylatable hydrocarbon and hydrogen.

14 Claims, 1 Drawing Figure

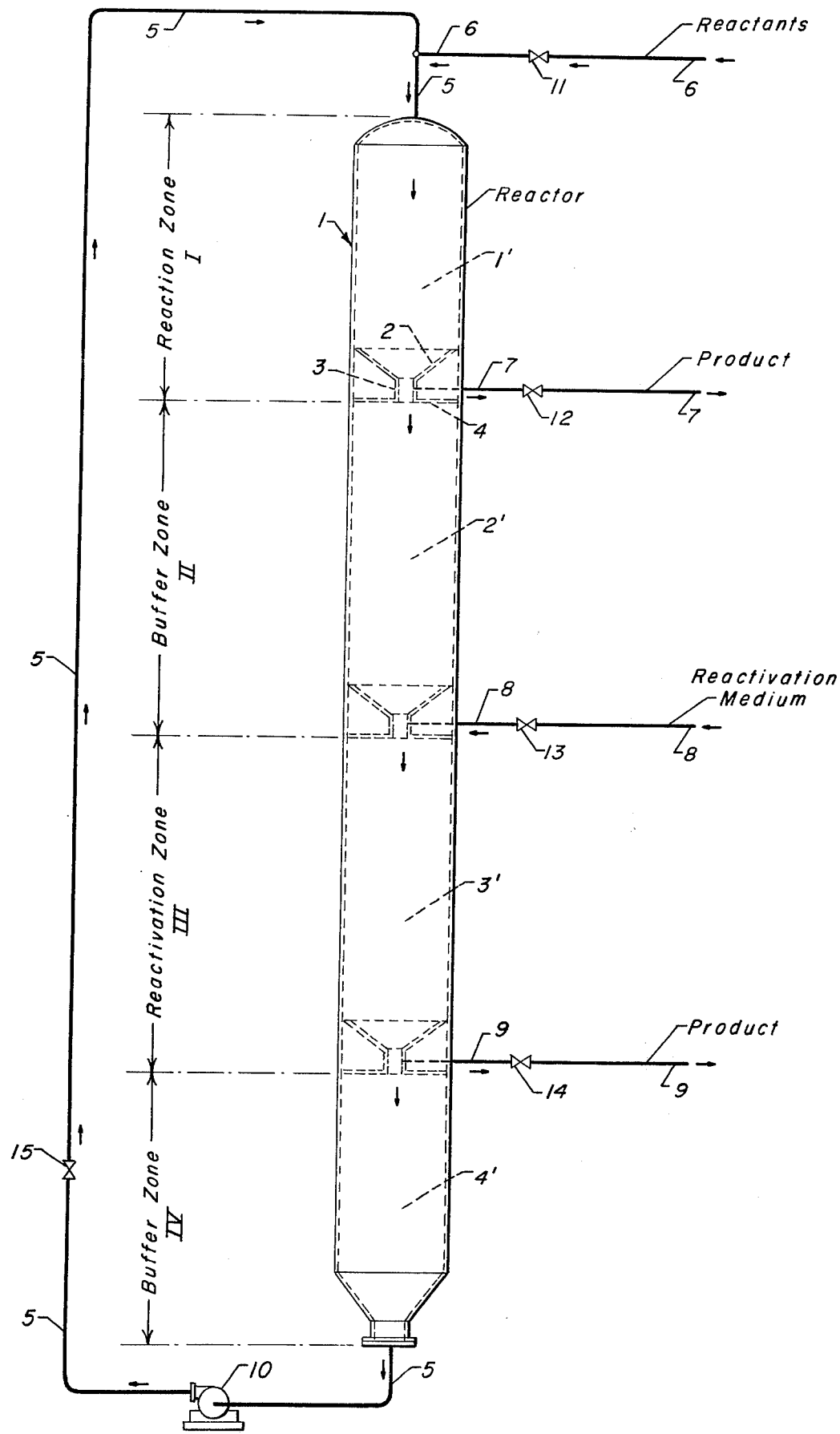

SIMULATED MOVING BED ALKYLATION PROCESS

BACKGROUND OF THE INVENTION

This invention relates in general to a continuous catalytic alkylation process utilizing a solid catalyst bed to effect an alkylation reaction, and more specifically, this invention relates to an application of a simulated moving catalyst bed utilizing a zeolitic catalyst to effect an alkylation reaction in one zone of a catalyst bed and a reactivation of the catalyst in another zone. Even more specifically, this invention relates to reactivating in an alkylation process a crystalline aluminosilicate zeolite catalyst composited with a Group VIII metal hydrogenation agent with a reactivation stream including hydrogen.

One of the problems in carrying out a catalytic reaction is that of catalyst deactivation. In essentially all catalytic reactions, over a period of time the catalyst will lose part of its activity. It is common practice to discard or reactivate a catalyst when its activity is sufficiently low to cause inefficiency or unprofitability, at which point, the catalyst is considered "spent". Various schemes are used to reactivate or regenerate a catalyst depending on catalyst characteristics, the process scheme, and economic considerations. Generally, the operation to regenerate a catalyst is considered unprofitable, although at least in certain processes, some, and even a great benefit is directly derived from a catalyst regeneration operation. When an operating plant must be taken out of service for the purpose of conducting a catalyst regeneration, and production time is lost, the economic liability is especially great. Typical examples of processes which require shutdown of normal operations to regenerate catalyst include naphtha reforming to high octane gasoline, hydrocracking, hydrodesulfurization, and di-olefin saturation, to name but a few, and in these processes, it is common for a plant to be shutdown about 2 to 10 percent of a calendar year for the purpose of catalyst regeneration. In other processes, the deactivation rate of the catalyst is so great that reactors may be installed in duplicate to allow normal operation in one, while regeneration or replacement of the catalyst in the standby reactor takes place. An example of such a process is a process for dehydrogenation of paraffins to olefins, but the technique of providing standby reactors or contactors is more common for simple operations like air drying. Another regeneration scheme is the recent development of continuous regeneration of a small portion of a catalyst bed by continuously removing a catalyst portion from the bed, regenerating it in continuous facilities external to the catalyst bed, and continuously returning regenerated catalyst to the catalyst bed. This method of catalyst regeneration has been successfully applied to a reforming process in which naphtha is upgraded to high octane gasoline. Still another regeneration technique is that commonly employed in fluid catalytic cracking units, wherein during normal operation of the process the entire catalyst bed is continuously moving between a reaction zone and a regeneration zone.

Each of the above described regeneration schemes has benefits and liabilities which make the scheme applicable to a given process and not another. The continuous schemes are becoming more desirable as processing severity increases, resulting in more rapid catalyst deactivation. From a historical viewpoint, it is seen that economics favor increasing reaction severity for many catalytic reactions, resulting in higher product yields and higher product quality, and a greater catalyst deactivation rate. While catalyst development has resulted in more active, more stable catalysts, an emphasis is being placed on maintaining essentially fresh catalyst activity throughout the duration of a catalyst run. In many processes, the increased value of a higher product yield or higher product quality throughout a catalyst run is greater than the increased cost of maintaining a higher catalyst activity, either through more expensive, more stable catalysts or through continuous regeneration schemes.

In the field of alkylation, essentially all existing plant capacity utilizes either hydrofluoric or sulfuric acid fluid catalysts. While it is an objective to develop a catalyst which will yield a higher quality alkylate product and a more economical process, it is also desirable to develop a catalyst which is safer to handle, less corrosive, and less objectionable from an environmental viewpoint than the present acid catalysts. Recent development work has led to several patents related to the use of aluminosilicate zeolite catalysts in alkylation processes, including U.S. Pat. Nos. 3,840,613, 3,549,557, 3,795,714, 3,417,148, 3,251,902, 3,851,004 and others. However, catalysts of the zeolite type suffer from losses of both activity and selectivity over a short period of operation in an alkylation process and require reactivation to maintain a suitable level of activity and selectivity. It has been generally concluded that rapid loss of activity has been the result of adsorption on the catalyst surface of polymeric and polyalkylated hydrocarbons. In U.S. Pat. No. 3,549,557, for example, it is shown that a zeolitic catalyst after about 10 hours or operation loses a substantial portion of its original selectivity and activity, but with periodic reactivation, the catalyst returns to almost original catalytic activity and selectivity. The reactivation procedure used in U.S. Pat. No. 3,549,557 is to stop normal operation of the alkylation process (which includes alkylation of isobutane and butylene at 195° F. and 500 psig.) by stopping olefin flow while continuing isobutane flow, raising the catalyst temperature to 600° F., at which temperature the catalyst is reactivated, lowering the catalyst temperature to alkylation conditions and reintroducing olefin feedstock. In U.S. Pat. No. 3,851,004, a zeolitic catalyst containing a hydrogenation agent of a Group VIII metal is used in an alkylation process, and a reactivation stream including hydrogen is incorporated to periodically reactivate the catalyst. Like the reactivation procedure shown in U.S. Pat. No. 3,549,557, the reactivation procedure of U.S. Pat. No. 3,851,004 is a cyclic one, in which reactants and reactivation media are alternately charged to a catalyst bed, thus requiring periodic and frequent stoppage of normal operation of the catalyst bed in its alkylation function.

SUMMARY OF THE INVENTION

Accordingly, it is an object of this invention to provide a processing scheme which will permit economic operation of an alkylation process utilizing a solid catalyst. Another object is to utilize a zeolite catalyst composited with platinum in an alkylation process. Still another object is to reactivate a zeolite catalyst composited with a Group VIII metal hydrogenation agent with a reactivation stream including hydrogen in an alkylation process.

A specific object of this invention is to provide a combination solid bed catalytic alkylation-catalyst reactivation process which will allow simultaneous, continuous reactivation of the catalyst in one zone while the catalyst bed is in normal operation in another zone.

In an embodiment, this invention relates to a continuous fixed bed catalytic alkylation reaction and catalyst reactivation process comprising the steps of: (a) providing a crystalline aluminosilicate zeolite catalyst composited with a Group VIII metal hydrogenation agent in a fixed bed containing four zones and having a fluid flow connecting path between said zones to interconnect said zones; (b) arranging said zones in a series and providing fluid flow connecting means between the last zone and the first zone of the series to provide a directional circular flow path through said zones; (c) providing a point between each two successive zones for introducing an inlet stream or withdrawing a product stream; (d) introducing a reactivation stream including alkylatable hydrocarbon and hydrogen at a first point located between two successive zones (zone II and zone III) to effect catalyst reactivation and to provide alkylatable hydrocarbon as a continuous component throughout said fixed bed of catalyst; (e) simultaneously withdrawing a first product stream from a second point located between said zone III and the next successive zone in the direction of flow (zone IV); (f) simultaneously introducing a reactants stream including an olefin-acting reactant into said fixed bed of catalyst at a third point located between said zone IV and the next successive zone in the direction of flow (zone I) to effect an alkylation reaction, a result of which is deactivation of said catalyst; (g) simultaneously withdrawing a second product stream from a fourth point located between said zone I and the next successive zone in the direction of flow (zone II); and, (h) periodically advancing downstream the points of charging said reactants stream and said reactivation stream, and the points of withdrawal of said product streams to the next successive point for introducing an inlet stream or withdrawing an outlet stream.

In another embodiment, the present invention relates to a continuous fixed bed catalytic alkylation reaction and catalytic reactivation process comprising the steps of: (a) providing a crystalline aluminosilicate zeolite catalyst composited with a Group VIII metal hydrogenation agent in a fixed bed containing three zones and having a fluid flow connecting path between said zones to interconnect said zones; (b) arranging said zones in a series and providing fluid flow connecting means between the last zone and the first zone of the series to provide a directional circular flow path through said zones; (c) providing a point between each two successive zones for introducing an inlet stream or withdrawing a product stream; (d) introducing a reactivation stream including alkylatable hydrocarbon and hydrogen at a first point located between two successive zones to effect catalyst reactivation and to provide alkylatable hydrocarbon as a continuous component throughout said fixed bed of catalyst; (e) simultaneously withdrawing a first product stream from a second point located between another two successive zones; (f) simultaneously introducing a reactants stream including an olefin-acting reactant into said fixed bed of catalyst at a third point located between the remaining two successive zones to effect an alkylation reaction, a result of which is deactivation of said catalyst; and, (g) periodically advancing downstream the points of charging said reactants stream and said reactivation stream, and the point of withdrawal of said product stream to the next successive points for introducing an inlet stream or withdrawing an outlet stream.

DETAILED DESCRIPTION OF THE INVENTION

The alkylation process of the present invention may be applied to the alkylation of isobutane, isopentane and similar isoparaffins. The preferred isoparaffins are isobutane and isopentane, particularly isobutane. A mixture of two or more isoparaffins may also be employed, if desired. Conventional isobutane alkylation feed stocks are suitable for use in the present process. Such conventional make-up isobutane feed stocks may contain some non-reactive hydrocarbons such as normal paraffins. For example, a conventional commercial isobutane alkylation feed stock generally contains about 95 weight percent isobutane, 4 weight percent n-butane and 1 weight percent propane. Mono-olefins which are suitable for use in the process of the present invention with the alkylatable isoparaffins stated above include $C_2$–$C_5$ olefins. Mixtures of two or more olefin compounds may also be employed in the present process with good results. For example, conventional olefin feed stocks used in commercial olefin alkylation operations contain mixtures of propylene and butylenes, butylenes and amylenes, or propylene, butylenes and amylenes. The benefits of the present process may be obtained using such feed stocks in combination with ethylene, as well as when using a single olefin. A $C_2$–$C_5$ olefin alkylation feed stock, which is particularly preferred for use in this process, may be derived from petroleum refining operations such as catalytic cracking and may therefore contain substantial amounts of saturated hydrocarbons, lighter and heavier olefins, etc.

Alkylation of isoparaffinic hydrocarbons, such as isobutane, isopentane and the like, with olefinic hydrocarbons such as propylene, butylene, amylenes, and olefin-acting compounds such as $C_2$–$C_5$ alkyl halides, etc., is well known as a commercially important method for producing gasoline boiling range hydrocarbons. The $C_5$–$C_{10}$ hydrocarbons typically produced by the isoparaffin-olefin alkylation reaction are termed "alkylate", which is particularly useful as a motor fuel blending stock because of its higher motor and research octane ratings, such that it can be used to improve the overall octane rating of gasoline pools to comply with the requirements of modern automobile motors. These high octane alkylate fuel components are particularly important in producing motor fuels of sufficient quality when it is desired not to employ alkyl lead compounds in the fuel to meet octane requirements.

The alkylation process of the present invention may also be applied to the alkylation of an alkylatable aromatic such as benzene, toluene, ethylbenzene, or cumene, a preferred alkylatable aromatic being benzene. Mono-olefins which are suitable for use in the present process with alkylatable aromatics such as those stated above include $C_9$–$C_{15}$ mono-olefins, the result of alkylation of these reactants being a $C_9$–$C_{15}$ side chain alkylaromatic hydrocarbon which is useful in the manufacture of detergents. A preferred feed stock includes a single alkylatable aromatic, especially benzene, combined with a mixture of $C_9$–$C_{15}$ mono-olefins.

Another application of the present process is the alkylation of benzene with ethylene to form ethylbenzene.

Still another application of the present process is the alkylation of benzene with propylene to form isopropylbenzene (cumene).

A suitable catalyst for the present process is an aluminosilicate zeolite catalyst composited with a Group VIII metal hydrogenation agent, preferably platinum. A description of the composition and preparation of a suitable catalyst is found in U.S. Pat. No. 3,851,004 as follows:

The crystalline zeolitic molecular sieves employed as one constituent of the catalyst composition of this invention are readily prepared from several synthetic crystalline zeolites well known in the art. Zeolite Y is especially preferred, but zeolite X, zeolite L, zeolite TMAΩ and acid treated, i.e., the hydrogen cation form of mordenite, are also suitable as is the naturally occurring mineral faujasite. A complete description of the composition and method of preparation of zeolite X, zeolite Y, zeolite L and H-mordenite are to be found, respectively, in U.S. Pat. Nos. 2,882,244, 3,130,007, 3,216,789 and 3,375,064. In those cases where the zeolitic molecular sieve starting material contains more than the permissible amount of alkali metal cations, such as sodium or potassium, the alkali metal cation content can be reduced by conventional ion exchange techniques whereby divalent, trivalent or tetravalent metal cations or monovalent nonmetallic cations such as hydrogen, ammonium, alkylammonium, and the like which can be thermally removed.

Preferably, in the typical case of zeolite Y which contains only sodium cations in the as-prepared state, the initial base exchange is carried out using an aqueous ammonium salt solution such as ammonium chloride, ammonium carbonate, ammonium sulfate or ammonium nitrate to the extent that the sodium cations are removed and replaced by ammonium ions to the extent that less than 3.5 weight percent (solids basis), remain. Thereafter, the zeolite is further contacted with an aqueous solution of one or more salts of polyvalent metal cations in proportions and of suitable concentration to exchange the desired equivalent percent of any residual sodium cations and/or ammonium cations for the polyvalent metal cations.

When the preferred zeolite Y has a $SiO_2$ to $Al_2O_3$ oxide molar ratio greater than 4 it is preferred that the alkali metal cation content of the finished catalyst is less than 0.25 and preferably less than 0.08 with respect to the equivalent mole ratio of the alkali metal oxide to aluminum oxide in the zeolite; however, it is not essential that polyvalent metal cations be present. Such zeolite compositions may be made by exchanging only a portion of the alkali metal of the original zeolite for thermally decomposable cations such as ammonium, alkylammonium or hydrogen, then heating at about 400° C. to 800° C., followed by further exchange of the alkali metal for such decomposable cations. These last introduced decomposable cations may then be decomposed to provide the low alkali metal cation form of the catalytic zeolite. This last calcination may optionally be the final calcination step in the catalyst preparation. This procedure for obtaining a low alkali metal cation content in a large pore crystalline zeolitic molecular sieve whereby 50 to 90 percent of the original alkali metal cations are exchanged for decomposable nonmetal cations and the intermediate is subjected to a thermal treatment above about 500° C. followed by further removal of the remaining alkali metal cations is known to increase the resistance of the zeolite's crystal structure to degradation at elevated temperature especially in the presence of water vapor. This double decationization procedure has also been called stabilization and the resulting low alkali metal cation zeolite product is sometimes referred to as an ultrastable form of the zeolite.

A preferred class of molecular sieves for use in the present process has a composition expressed in terms of mole ratios of oxides as:

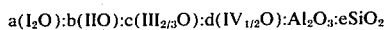

$$a(I_2O):b(IIO):c(III_{2/3}O):d(IV_{1/2}O):Al_2O_3:eSiO_2$$

where I represents a monovalent metal cation; II represents a divalent metal cation; III represents a trivalent metal cation; IV represents a tetravalent cation; $a$ has a value of from zero to 0.25 preferably zero to 0.08; $b$ has a value of from zero to 0.65; $c$ and $d$ each have values of from zero to 1; $e$ has a value of from 2 to 20, preferably 4 to 15; with the proviso that when $e$ has a value of from 2 to 3, the value of $(b+c)=0.75$ to 1, preferably 0.75 to 0.85, and $d=0$; and with the proviso that when $e$ has a value of > 3 to 4, the sum of $(b+c+d)=0.6$ to 1.0, preferably 0.6 to 0.85. The monovalent cations represented by (I) in the zeolite composition formula of the immediately preceding paragraph are usually sodium or potassium or a mixture thereof, but other monovalent metal cations such as lithium, rubidium and cesium are permissible. The divalent metal cations represented by (II) are preferably selected from Group IIa of the Periodic Table (Handbook of Chemistry and Physics, 47th Edition, page B-3, Chemical Rubber Publishing Co., U.S.A.) especially magnesium, calcium, strontium and barium, but manganese, cobalt and zinc can also be used. The trivalent metal cations represented by (III) of the formula can be aluminum, chromium and/or iron, and/or the trivalent rare earth cations, lanthanium, cerium, praesodymium, neodymium, samarium, gadolinium, europium, terbium, dysprosium, holmium, erbium, thulium, ytterbium and lutetium. The tetravalent metal cations represented by IV are exemplified by thorium and cerium.

The Group VIII metals employed as hydrogenation agents, i.e., nickel, platinum, palladium, rhodium or ruthenium, can be used singly or in combination with each other or in combination with other metals having hydrogenation activity. The quantity of the Group VIII metals, specified above, present in the catalyst composition is not narrowly critical, but should be at least about 0.05 weight percent based on the weight of dehydrated zeolite. The upper limit in weight percent in the use of platinum, palladium, rhodium and ruthenium is usually set at about 2, mainly because of economic practicality, in view of the high cost of these metals and because larger amounts do not produce significantly improved results. Nickel, being relatively cheap, can be used, if desired, in greatly increased amounts, but more than about 20 weight percent imparts no further improvement to the process. The metal hydrogenation agents can be combined with the zeolitic molecular sieve by any of various techniques such as impregnation of the molecular sieve with a salt of the noble metal usually from a solution of the salt in a suitable aqueous or nonaqueous solvent or by an ion-exchange technique. When desired, the non-noble metal may also be incorporated by impregnation and/or adsorption of a decomposable compound, and/or by ion-exchange technique. Satisfactory methods for loading these metals on the molecular sieve are disclosed in U.S. Pat. Nos. 3,013,982, 3,013,987 and 3,236,762. The preferred technique for combining the Group VIII noble metal with the molecular sieve is that wherein an aqueous solution of the noble metal as an amine complex cation is employed in an ion-exchange method as disclosed in U.S. Pat. No. 3,200,082.

The combining of the metal hydrogenation agent with the molecular sieve may be done during or after the treatment of the zeolite for the purpose of modifying its original cation form to that corresponding to the active composition specified hereinabove or can be done after the zeolite has been diluted and bindered as described hereinafter. It has been found preferable to combine the hydrogenation metal with the zeolite during or after the last treatment wherein the alkali metal cation content of the zeolite is brought down to its final level. Thus, when the double decationization procedure is employed in the preparation of the zeolite specified composition, the hydrogenation metal or metals are preferably combined with the zeolite during or after the non-metal ion-exchange treatment for further alkali metal removal.

Thereafter, the molecular sieve combined with the hydrogenation metal is calcined in air at a temperature in the range of 400° to 800° C., preferably 450° to 650° C. This treatment converts the metal to an active form and drives off decomposition products from ammonium or other decomposable compounds that may be present from the cation exchanging and metal loading treatments. If desired, this calcination may be done after any catalyst pellet molding or tableting treatment, with the further benefit of strengthening the catalyst body.

Except for the aforesaid Group VIII metal hydrogenation agent, it is not necessary to employ any additional or conventional catalysts or promoters in conjunction with the low alkali metal zeolitic molecular sieve in the practice of this invention but it is not intended that such compositions be necessarily excluded. Any catalytically active metal or compound thereof can be present either on the external surface or internal cavities of the zeolite or otherwise carried on diluents or binders used to form agglomerates of the catalyst. Suitable diluent materials in the catalyst composition include sintered glass, asbestos, silicon carbide, fire brick, diatomaceous earths, inert oxide gels such as low surface area silica gel, silica-alumina cogels, calcium oxide, magnesium oxide, rare earth oxides, alpha alumina and clays such as montmorillonite, attapulgite, bentonite and kaolin, especially clays that have been acid washed.

It has been found that zeolite catalysts utilized in an alkylation reaction deactivate rapidly but can be reactivated by passing alkylatable hydrocarbon over the catalyst in the absence of olefin-acting reactant. It has also been found that reactivating the zeolite catalyst at a temperature at least 25° F. higher than the reaction temperature is effective in reactivating the catalyst, and that reactivation of a zeolite catalyst composited with a Group VIII metal activator by a hydrocarbon stream in which hydrogen is dissolved is effective. A typical blocked out operation incorporating the stated regeneration concepts would result in a discontinuous operation wherein reactants are charged to and reaction products withdrawn from the catalyst bed for a period of time, followed by a catalyst reactivation period, followed by another period of operation, etc. The present process, utilizing a catalyst described hereinabove and a reactivation medium including alkylatable hydrocarbon and hydrogen, is a continuous reaction and reactivation process wherein reactants and reactivation medium are continuously introduced into and products are withdrawn from the process.

An understanding of this invention may be aided by reference to the accompanying drawing which represents a schematic flow diagram of an embodiment of the inventive process. The present invention concerns application of a simulated moving bed technique described in U.S. Pat. No. 2,985,589 and others to a catalytic process in which a catalytic reaction and a reactivation of the catalyst employed take place in different zones of a catalyst bed. Referring to the accompanying diagram, a suitable arrangement of apparatus in simplified form is illustrated for carrying out the process of this invention. Any suitable apparatus comprising a series of fixed catalyst sub-beds having a point for introducing a feed stream or withdrawing a product stream between sub-beds, having a fluid-flow connecting path between the outlet of one sub-bed and the inlet of its next adjacent sub-bed, having fluid flow connecting means between the outlet of the last sub-bed and the inlet of the first sub-bed to serially interconnect the sub-beds of catalyst in a circular manner, and comprising a suitable means, such as a valve or manifold, for shifting the points of inlet and outlet for the various feed and product streams involved in the process may be provided. It is also within the scope of this invention that a single vertical, continuous bed of catalyst having vertically disposed multiple points to introduce feed streams or withdraw product streams, having fluid flow connecting means between the bottom and the top of the catalyst bed to serially interconnect the catalyst bed in a circular manner, and comprising a suitable means, such as a value or manifold, for shifting the points of inlet and outlet of the various feed and product streams involved in the process may be provided. In this description, the term catalyst "bed" refers to the entire amount of catalyst loaded in the reactor, however, the bed may be divided into smaller units of essentially equivalent catalyst volume which are herein designated as "sub-beds". The accompanying diagram illustrates a preferred apparatus design, being particularly suitable because of its compact arrangement of the series of fixed sub-beds in adjacent, superadjacent and subadjacent relationship to each other. The series of fixed sub-beds, such as sub-beds 1'−4', may be a number of horizontally disposed, separate beds interconnected by a pipe between the bottom of one sub-bed and the top of its downstream adjacent sub-bed, or the sub-beds may be stacked one upon another, within a suitable vertical column, as illustrated in the accompanying diagram. The sub-beds herein are placed in their entirety in reactor 1, which contains suitably shaped partitioning means to divide the vertical column into a series of adjacent sub-beds, each sub-bed being divided from its adjacent sub-bed by a funnel-shaped partitioning member such as partition 2 in sub-bed 1', having a downcomer 3 of restricted cross-sectional area in open communication with an outlet nozzle 7 and opening into a subadjacent sub-bed 2' through a transverse partitioning member 4 which comprises the upper boundary of said adjacent sub-bed 2'. Other partitioning means such as those described in U.S. Pat. Nos. 3,208,833 and 3,214,247 are also suitable.

The advantages of constricting the width of the bed at the entry and withdrawal points of the various streams are: (1) prevention of convective back-mixing of fluid in a direction opposite to the direction of fluid flow and, (2) greater ease of distributing fluids flowing into and out of the reactor because of the ability to thereby eliminate channeling and other undesirable loss of uniform distribution.

The process to which the accompanying diagram is directed is described by reference to a particular arrangement of multiple beds of fixed or stationary solid catalyst and to a process operated under essentially liquid phase conditions, but it will be understood that other arrangements of beds, vapor or gaseous phase operation, and the use of other types of equipment are also contemplated within the broad scope of the present invention.

Although the solid catalyst is described as being distributed in a plurality of fixed beds, it is obvious that the series of interconnecting zones actually constitutes a continuous, vertical bed interconnected by conduits of reduced cross-sectional area. A fluid pump is provided between at least one pair of adjacent beds to provide a positive, unidirectional (downstream) flow of fluid. One of the essential characteristics of the process is that a continuously flowing stream of fluid (either liquid or vapor phase) is circulated through the series of beds from the first to the last in the series, to which stream, which is herein designated as the internal fluid, at least two inlet feed streams are introduced and at least one outlet product stream is withdrawn.

The terms "upstream" as used herein indicate points of reference relative to the flow of the internal fluid stream countercurrent to the apparent flow of the solid particles of catalyst, a point upstream designating a point in the continuous flow of fluid already passed and a point downstream designating a point in the stream of fluid yet to be contacted. Since the flow of hydrocarbons is countercurrent relative to the solid catalyst, a point downstream in the direction of fluid flow is, in effect, upstream in the simulated flow of catalyst, which is made to appear to flow by periodically moving the points of introduction of inlet streams and points of withdrawal of product streams in the same direction as the flow of internal fluid through the column. Although some minor variation is allowable, the change in location of all inlet and outlet streams occurs essentially simultaneously and the shift in location of each inlet and outlet stream is in a downstream direction essentially an equal distance. A simulated moving catalyst bed effect is thus achieved, and the effect becomes cyclic as the points of inlets and outlets advance in a downstream direction until the original reference point is reached, ending a given cycle. Accordingly, the present process is herein characterized as a "cyclic" and "continuous" process. It is thereby intended to define a method by which the various feed and product streams are charged into and withdrawn from the system in a continuous manner, without interruption, with respect to either the flow rate or composition of the several streams, and the points of introduction of inlet streams and the points of withdrawal of product streams are advanced in a downstream direction with regard to the internal fluid flow within the system. Although the solid catalyst remains in fixed position, a simulated countercurrent flow arrangement is thereby established, since incoming feed is contacted at its point of introduction with catalyst relatively fresh in comparison with downstream contacting zones.

For the purpose of this description, the boundary of a "zone" is defined by successive fluid inlet streams into and outlet streams from the catalyst bed. A zone will always be in the same relative position in relation to inlet and outlet streams, and may contain catalyst, void space, partitions, distributors, and other equipment. A typical arrangement of the several zones comprising the present process for the operation of a continuous, simulated countercurrent flow, fixed bed process at a given instant of the process cycle is illustrated in the accompanying diagram, a reactant mixture being introduced into the farthest upstream point of the so-called "reaction zone" (zone I) of the process, the reaction zone being relatively upstream with respect to a "buffer zone" (zone II), from which a product stream is withdrawn, the latter being upstream with respect to a "reactivation zone" (zone III) into which a reactivation stream is introduced, and the reactivation zone being upstream with respect to a secondary buffer zone (zone IV) from which a second product stream is withdrawn. Because of the cyclic flow of fluid within the process, the secondary buffer zone is also upstream with respect to the aforementioned first zone in series, that is, the reaction zone.

It is to be noted that the stage of the cycle illustrated is shown for illustrative purposes only to indicate the relationship of the various feed and product streams and the flows of the various streams at the particular instant that the zones occupy the positions shown. In the illustration, the reaction zone occupies sub-bed 1', the buffer zone occupies sub-bed 2', the reactivation zone occupies sub-bed 3', and the secondary buffer zone occupies sub-bed 4'; at a subsequent stage of the cycle, for example, after the first downstream shift of the points of introduction of the inlet streams and the points of product streams withdrawal, the reaction zone occupies the portion of catalyst bed previously comprising the buffer zone, the latter zone occupies the portion of catalyst bed formerly comprising the reactivation zone, the reactivation zone occupies the portion of catalyst bed formerly comprising the secondary buffer zone, and the latter zone occupies the portion of catalyst bed formerly comprising the reaction zone.

In the stage of the cycle illustrated, reactants enter the pump-around line 5 via line 6 and are introduced into the top of sub-bed 1', a product stream is withdrawn via line 7 at a locus at the top of sub-bed 2', a reactivation stream is introduced into the top of sub-bed 3' via line 8 and a second product stream is withdrawn via line 9 at a locus at the top of sub-bed 4'. In order to maintain the present process on a continuously cyclic basis, fluid removed from the bottom of sub-bed 4' is pumped into the top of sub-bed 1'. This stream is referred to as pump-around fluid and continuously varies in composition and flow rate, depending upon the function of the bottom catalyst sub-bed in the particular stage of the cyclic operation. From the bottom of sub-bed 4', a pump-around fluid is withdrawn via line 5, and is pumped via pump-around pump 10 to the top of the reactor 1 where it enters sub-bed 1' together with the reactants stream. The flow rates of the inlet, outlet, and pump-around streams are controlled by the corresponding valves 11, 12, 13, 14 and 15. After a suitable period of operation, the points of introduction or withdrawal of the reactants, product, and reactivation streams are advanced to the next downstream points of inlet or outlet, i.e., the reactants stream is introduced into reactor 1 via line 7, the product stream is withdrawn via line 8, the reactivation stream is introduced via line 9, and the second product stream is withdrawn via line 6. After a second suitable period of operation, the streams are advanced again to the next downstream point of inlet or outlet, and after a third and a fourth suitable period of operation and a third and a fourth advancement of the streams, the streams will be in their reference positions shown in the accompanying diagram, and a full cycle will be complete.

An important part of the present invention, important that is, to the realization of the type of flow provided by the present method of operation, is the provision of a suitable programming device for changing the points of inlet and outlet into and from the reactor and for advancing these in a downstream direction during the operation of the process. While it is preferred that the advancement of all streams is both simultaneous and equal in distance, the scope of the present inventive concept is not limited to simultaneous advancement of the stream. Any suitable form of fluid distribution center, such as a manifold arrangement of valves and incoming and outgoing lines may be provided with timed, electrically operated switches to open and close the appropriate valves. The programming principle may also be suitably effected by means of a rotary plug valve of particular design as illustrated in U.S. Pat. No. 2,985,589 and others, however, the specific means for changing the inlet into and outlet from the reactor zones, and advancing the points of introduction of inlet streams and the points of withdrawal of product streams is not essential to the present invention.

In the present description, the reactor, catalyst inlet and outlet points, etc., are referred to in their entirety as the "reactor system". Referring to the attached drawing, a reactant stream is introduced into the reactor system, is admixed with the internal fluid, and is introduced into the first (farthest upstream) sub-bed of the reaction zone. Depending on the rate of reaction, volume of catalyst present in each sub-bed, and operating conditions, one or more sub-beds up to about 20 are required in the reaction zone to carry out the reaction to the desired completeness. In the reaction zone, a polymeric material, coke, adsorbed reactant, adsorbed reaction product, etc., adheres to the catalyst and is maintained in adherence with the catalyst as the zones pass through the catalyst bed, i.e., as the catalyst flows in simulated motion countercurrent to the internal fluid flow. The material adhering to the catalyst is swept into the secondary buffer zone together with a portion of the non-adhering components of the internal fluid as a result of the advancement of inlet and outlet streams. Referring to the attached drawing, catalyst sub-bed 1' is the reaction zone at the instant illustrated. The instant following advancement of the inlet and outlet streams, the internal fluid occupying the former reaction zone will be in the secondary buffer zone (zone IV). In zone IV, the material adhering to the catalyst continues to do so, but the non-adhering material is swept back into the reaction zone by force of the internal fluid flow through zone IV. Accordingly, there is a composition gradient of the non-adhering material in a downstream direction through zone IV, which contains a sufficient number of catalyst sub-beds to provide the desired content of the non-adhering material at the top of the first sub-bed of zone IV. About 1 to 20 catalyst sub-beds are needed in zone IV. It is also evident that reaction is initiated in zone IV, as reactant is introduced into zone IV by advancement of the inlet and outlet streams. At the bottoms of the last (farthest downstream) sub-bed of the reaction zone, a portion of the internal fluid is withdrawn as a product stream and passed to a suitable separation zone wherein the components are separated as desired. The internal fluid at the downstream end of the reaction zone includes reaction products and unreacted reactants; the portion not withdrawn in the product stream passes into the buffer zone (zone II). Depending on the operating conditions of zone II, it may be utilized to either prevent or allow passage of reaction products and unreacted reactant components into the reactivation zone (zone III). In the former case, which is designated as "negative flow", relatively more catalyst sub-beds are required than in the latter case, but in both cases, about 1 to 20 sub-beds are required. Reaction products and unreacted reactants are prevented from passage into zone III by suitable control of the flow rate of internal fluid in zone II in relation to the void volume between catalyst particles and the frequency of advancement of inlet and outlet points of the reactor system. An advancement rate may be determined by dividing the void volume between catalyst particles of a zone by the time interval of advancement of the inlet/outlet point from the upstream side to the downstream side of that zone. When the advancement rate is greater than the internal fluid rate at zone II, the effect is a simulated co-current flow of catalyst and fluid in zone II; i.e., reactivation medium is withdrawn as part of the product stream because the points of inlet/outlet are advanced faster than the catalyst void volume is swept of reactivation medium. When the advancement rate is slower than the internal fluid rate of zone II reaction products and unreacted reactants pass through zone II and enter zone III, in which case flow is designated as "positive". When the rates are equal, a simulated plug or "balanced" flow is effected to maintain separate the components of zone I and zone III. By the same mechanism, it is possible to control flow in zone IV to achieve either positive or negative flow. At the downstream boundary of zone II, a reactivation medium is introduced into the system to reactivate the catalyst in zone III, i.e., to remove the catalyst particles the material adhering to and deactivating the catalyst as described hereinabove. About 1 to 20 sub-beds of catalyst are required to effect the desired catalyst reactivation. Downstream of the reactivation zone, a second product stream including reactivation medium and the material adhering to the catalyst is withdrawn to suitable fractionation.

Because a specific application of the present process may require little or no separation of the fluid components of the reaction and reactivation zones, i.e., the fluid components of the reaction and reactivation zones are intermixable without degradation of either product or catalyst, only a single product outlet stream may be provided, located immediately downstream of either the reaction or reactivation zone. In this case, the process comprises a reaction zone, a reactivation zone, and a single buffer zone. Especially preferred is a 3 zone process comprising in series a reaction zone followed by a reactivation zone followed by a buffer zone, and because of the cyclic nature of the process, followed by the reaction zone. Similarly, a 3 zone process comprising a reaction zone followed by a buffer zone followed by a reactivation zone is within the scope of the present invention. Flow in the buffer zone of a 3 zone process may be either positive, negative, or balanced. In an embodiment wherein flow through the buffer zone is positive, fluid components of the reaction and reactivation zones are intermixed whereas in an embodiment wherein negative flow is effected in the buffer zone, fluid components of the reaction zone or the reactivation zone, whichever is immediately downstream of the buffer zone, pass into the third zone, but the components of the zone upstream of the buffer zone do not pass into the zone downstream of the buffer zone.

The present inventive process requires as a minimum two inlet streams including a reactant stream and a reactivation stream, and one outlet product stream. Therefore, by the present definition of a zone as being bounded by successive inlet and outlet streams, the minimum number of zones is three. One skilled in the art will recognize the desirability of adding inlets or outlets to allow passage into or out of the reactor of additional streams. For example, but not as a limitation, reactant and reactivation streams may be introduced into the reactor system in multiple downstream injection points, inert purge streams may be introduced into a buffer zone, etc. Each additional inlet or outlet greater than the minimum of three will result in the additional zone in the reactor. In a specific application of the process 3, 4, 5 or more zones may be desirable.

Each zone of the reactor may contain a portion of a single bed of catalyst, or, in a preferred mode of operation, each zone may contain a plurality of 1 to 20 sub-beds, each sub-bed having an identical configuration and an essentially equivalent quantity of catalyst. The advantage of providing a plurality of catalyst sub-beds within a zone as compared with a single catalyst bed within a zone lies in the resulting increase in continuity in the process in the respect that the composition of the internal fluid stream at any point within a zone is maintained within a narrower range of fluctuation as the number of catalyst sub-beds increases while the catalyst content within a zone remains constant. However, increasing the number of sub-beds requires greater capital investment. Each sub-bed is bounded by a point to allow introduction of a reactivation stream or reactants stream, or withdrawal of a product stream. In the simplest embodiment, such a point for introduction of an inlet stream or withdrawal of a product stream comprises a nozzle welded to the reactor shell and drilled out to provide open communication through the nozzle to the fluid flowing within the reactor. In a preferred arrangement, each sub-bed is separated from its adjacent sub-bed by fluid collection means described hereinabove.

With zones of a reactor configuration as shown in the attached drawing, i.e., in adjacent, superadjacent, and subadjacent relationship to each other, it is a requirement of the present invention to pass the fluid removed from the bottom of the bottommost zone to the top of the uppermost zone. This is done by means of a pump when the fluid is liquid, or a compressor when the fluid is gaseous, the fluid stream being referred to as a pump-around stream and allowing the process to operate on a cyclical basis. Adjustment of the pumparound rate must be made in accordance with a desired flow rate through a specified zone of the reactor, and will determine an internal fluid flow rate in the reactor, this internal flow rate being a different rate in each zone as inlet and outlet streams are introduced into and withdrawn from each zone.

While the illustration in the attached drawing shows the countercurrent flow pattern with catalyst moving in a simulated upward direction and fluid flowing through the catalyst bed in a downward direction, and the advancement of inlet and outlet streams in a downward direction, a countercurrent flow in an opposite direction may also be achieved by withdrawing fluid to the pump around circuit from the top of the reactor and passing it into the bottom of the reactor, thereby creating an upward fluid flow in the reactor, and advancing the position of the inlet and outlet streams in a downstream direction which will now be in an upwardly direction.

The fluid flow rate in a reactor of the present process is adjusted to provide a charging rate consistent with maintenance of fixed bed conditions, which is dependent upon whether gas phase or liquid phase contacting is utilized, the size of the particles of catalyst, the degree of packing of catalyst in the confines of the bed, and the direction of flow. When utilizing gaseous feed stocks and displacing agents, the fluid flow rate in the reactor is below the rate at which fluidization of the catalyst particles occurs, at a rate preferably not in excess of about 3000 volumes/hour of internal fluid per volume of catalyst, more desirably at a rate of from about 0.06 to 600 volumes/hour of internal fluid per volume of catalyst. When utilizing liquid phase contacting conditions, fluid flow rate is desirably not greater than about 50 volumes/hour of fluid flow per volume of catalyst and more desirably from about 0.01 to 30 volumes/hour of fluid flow per volume of catalyst. These rates are, of course, dependent upon the size of the catalyst particles, the depth and width of the beds, specific processing conditions, and mechanical design of the apparatus. When catalyst completely fills the reactor, the limiting rate of flow of fluid through each bed is set by the free or "void" space between particles of catalyst, the space thus provided establishing a maximum accommodation flow for any given pressure differential, but which may be increased if a greater pressure differential is tolerable. The finer the particles of catalyst, the greater the pressure drop through each bed, resulting in an ultimate permissible flow rate being fixed as the rate which does not give rise to a pressure drop through all of the beds greater than the discharge pressure delivered by the circulating fluid pump.

Advancement of the inlet and outlet streams of the present invention is made from one point to the next successive point for introducing or withdrawing a stream, the time interval between advancement from one point to the next successive point being referred to as an advancement speed. In a cycle, each inlet stream is introduced and each product stream is withdrawn through each inlet/outlet point provided, and is advanced in a timed sequence at a predetermined cycle rate, i.e., the time required to complete one cycle. The cycle rate is about 5 minutes to 24 hours, with a preferred cycle rate of about 5 minutes to 3 hours. For example, in a reactor system comprising 20 catalyst sub-beds, 20 points are provided to introduce or withdraw a stream; a cycle rate of 60 minutes results in advancement of the inlet/outlet streams every 3 minutes. The advancement speed may vary slightly from one sub-bed to another, but it is preferred that the advancement speed be equal for all sub-beds.

In the present inventive process, the reactivation stream includes alkylatable hydrocarbon and hydrogen. Preferably, the alkylatable hydrocarbon is in a liquid phase and hydrogen is present in a saturation quantity or less. A hydrogen/alkylatable hydrocarbon mole ratio of about 0.001/1 to 1/1 is desired in the reactivation stream, but preferably hydrogen addition is controlled such that the solubility level of the internal fluid at any point in the reactor system is not exceeded. Hydrogen may also be introduced into the reactivation zone as a gas in an inlet other than the one in which alkylatable hydrocarbon is introduced. The reactant stream includes olefin-acting reactant alone or in admixture with alkylatable hydrocarbon. Preferably, it too is in a liquid phase. In a preferred mode of operation wherein a balanced or negative flow is effected in an adjacent buffer zone upstream of a reaction zone, alkylatable hydrocarbon is required in admixture with olefin in the reactant stream so that a satisfactory molar ratio of alkylatable hydrocarbon/olefin is achieved in the reaction zone. To provide alkylatable hydrocarbon in sufficiently high quantity, it is desirable to recycle at least a portion of a product stream to the reactant stream, and introduce the admixture into the reactor system. In a 4 zone system as described hereinabove, it is preferred to recycle at least a portion of the product stream forming the downstream boundary of the reaction zone. By achieving a sufficiently high alkylatable hydrocarbon/olefin ratio in the reaction system, olefin oligomerization is suppressed. In a three zone system, only a portion of the product stream may be recycled; the remaining portion must be withdrawn as net product. A molar ratio of alkylatable hydrocarbon/olefin of about 1/1 to 200/1 in the admixed internal fluid and reactant streams at the point of introduction of olefin reactant into the reaction zone is preferred; especially preferred is a molar ratio of about 30/1 to 100/1. Such a relatively high alkylatable hydrocarbon/olefin ratio is achieved by control of the internal fluid flow rate, recycle of production described hereinabove, and introduction of fresh alkylatable hydrocarbon in the reactant stream. Relative to the olefin introduced in the reactant stream, the internal fluid flow rate at the point of introduction of olefin reactant is controlled to provide alkylatable hydrocarbon at a molar ratio of 1/1 to 200/1; the product recycle rate is controlled to provide alkylatable hydrocarbon at a molar ratio of 0/1 to 200/1; and introduction of fresh alkylatable hydrocarbon in the reactant stream is also controlled to provide alkylatable hydrocarbon at a molar ratio of 0/1 to 200/1. To obtain a predetermined alkylatable hydrocarbon/olefin ratio at the point of reactant stream introduction into the reaction zone, it is necessary to judiciously balance the amount of alkylatable hydrocarbon provided by the three sources stated above; as an illustration, but not as a limitation, a molar ratio of alkylatable hydrocarbon/olefin in the admixed internal fluid and reactant streams of 100/1 may be achieved by controlling the internal fluid flow rate to result in a 10/1 ratio, fresh alkylatable hydrocarbon may be supplied in the reactant stream at a 10/1 ratio, and product recycle to the reactant stream may be controlled to result in an 80/1 ratio. Alkylatable hydrocarbon introduced into the reactor system in the reactivation stream may also be controlled by relating it to olefin introduced in the reactant stream. In this case, a molar alkylatable hydrocarbon/olefin ratio of about 1/1 to 100/1 is preferred.

Operating conditions in the reactor include a temperature in the reaction zone of about 100° to 400° F., preferably 150° to 250° F. a temperature in the reactivation zone of about 100° to 600° F., preferably 150° to 300° F., pressure sufficient to maintain liquid phase, about 10 to 50 atmospheres, and a total catalyst volume of 0.1 to 100 times the volume/hour of olefin-acting reactant introduced into the reactor system.

PREFERRED EMBODIMENT

In a preferred embodiment of the invention, a simulated moving bed reactor system is applied to an alkylation reaction of a mixture of butenes with isobutane to produce a motor fuel alkylate product. A reactor system containing four vertical, adjacent zones of a crystalline aluminosilicate zeolite catalyst composited with a Group VIII metal hydrogenation agent as described hereinabove is provided with internal fluid flow in a downward direction through said zones. A simulated catalyst movement in an upward direction is effected. Into the upstream end of a reaction zone (zone I), a reactant stream including principally butenes and isobutane is introduced together with an isobutane rich internal fluid flowing from an adjacent secondary buffer zone, this fluid being the pump-around fluid whenever the reaction zone is an uppermost position in the reactor. Downstream of the reaction zone, a product stream including principally isobutane, alkylate, and unreacted olefin is withdrawn to a fractionation zone, said product stream forming the downstream boundary of the reaction zone and the upstream boundary of an adjacent primary buffer zone. In the former zone, a reaction and partial separation of reactants takes place as the olefin is adsorbed in the pores of the catalyst, and during subsequent part of a cycle is carried into the secondary buffer zone (zone IV) upstream of the reaction zone. It is conjectured the rapid loss of activity observed in the reaction zone results from a polymeric hydrocarbon forming in the reaction zone and adhering to the catalyst surface. In the primary buffer zone (zone II), the internal fluid flow rate is controlled to be equal to the rate of advancement of the inlet and outlet streams into and out of the reactor system when the rate of advancement is expressed as the rate of flow of catalyst void volume, i.e., the volume between particles of catalyst, as described hereinabove. Accordingly, fluid flow in zone II is balanced. The internal fluid stream flowing downstream through the primary buffer zone of the process is admixed at the downstream boundary of that zone and the upstream boundary of an adjacent reactivation zone (zone III) with an inlet stream of reactivation media including principally isobutane saturated with hydrogen. In this preferred embodiment, it is surmised that the hydrogen acts to hydrogenate the polymeric hydrocarbon formed in the reaction zone, thereby lessening its adherence to the catalyst. The reactivation stream also acts as a displaying agent to displace olefin adsorbed in the catalyst pores and polymeric hydrocarbon adhering to the catalyst, thereby reactivating the catalyst. The displacing action is primarily a mass action effect and requires a molar ratio of isobutane in the reactivation stream to olefin in the reactants stream of about 1/1 to 100/1. As the internal fluid passes downstream through the reactivation zone, it becomes enriched in alkylate and unreacted olefin, both of which enter the reactivation zone with the catalyst from zone IV as a result of advancement of inlet and outlet streams. At the downstream boundary of the reactivation zone, which is also the upstream boundary of an adjacent secondary buffer zone (zone IV), another product stream including principally isobutane, alkylate product, and unreacted olefin is withdrawn to the fractionation zone, wherein alkylate product is separated and recovered. Internal flow in zone IV may be positive, negative, or balanced, but in a preferred mode of operation flow it is maintained negative. Olefin concentration in the secondary buffer zone increases in a downsteam direction, and with isobutane available in the internal fluid stream, reaction begins to take place in that zone, reaching the highest degree of reactivity at the point of introduction of the olefin-containing reactant stream. Operating conditions in the reactor include liquid phase operation, with sufficient pressure of about 10 to 30 atmospheres to obtain liquid phase, a ratio in the reactants stream of isobutane/olefin of about 1/1 to 100/1 by volume, and temperature in the reaction and reactivation zone of about 100° to 400° F., preferably 150° to 250° F. A complete cycle rate of about 10 minutes to 6 hours is preferred. Each zone contains 1 to 20 sub-beds of catalyst, the total catalyst bed having a liquid hourly space velocity (volume per hour of olefin reactant-/volume of catalyst inventory) of about 0.01 to 10. In a particularly preferred embodiment, the reaction zone, primary buffer zone, reactivation zone, and secondary buffer zone contain 2, 2, 18 and 2 sub-beds of catalyst, respectively. In this embodiment of the present invention, it is preferred that at least a portion of the product stream withdrawn from the reactor system between zones I and II is recycled to the reactor system by admixing it with the reactants stream and introducing the admixture into the reactor system between zone I and zone IV, as described hereinabove. Isobutane/olefin ratio in the stated product stream is substantially higher than that of the reactants stream, therefore recycling a portion or all of the stated product stream has the effect of increasing isobutane/olefin ratio in the reactants stream. It is considered that oligomerization of olefin decreases as isobutane/olefin ratio increases, therefore recycling of the stated product stream has the beneficial result of reducing oligomer production. When all of the stated product stream is recycled, the product stream withdrawn between zones III and IV represents the net effluent of the reactor system.

We claim as our invention:

1. A continuous fixed bed catalytic alkylation reaction and catalyst reactivation process comprising the steps of:
   a. providing a crystalline aluminosilicate zeolite catalyst composited with a Group VIII metal hydrogenation agent in a fixed bed containing four zones and having a fluid flow connecting path between said zones to interconnect said zones;
   b. arranging said zones in a series and providing fluid flow connecting means between the last zone and the first zone of the series to provide a directional circular flow path through said zones;
   c. providing a point between each two successive zones for introducing an inlet stream or withdrawing a product stream;
   d. introducing a reactivation stream including alkylatable hydrocarbon and hydrogen at a first point located between two successive zones (zone II and zone III) to effect catalyst reactivation and to provide alkylatable hydrocarbon as a continuous component throughout said fixed bed of catalyst;
   e. simultaneously withdrawing a first product stream from a second point located between said zone III and the next successive zone in the direction of flow (zone IV);
   f. simultaneously introducing reactants consisting essentially of isobutane or isopentane or a mixture thereof and at least one $C_2-C_5$ olefin into said fixed bed of catalyst at a third point located between said zone IV and the next successive zone in the direction of flow (zone I) and reacting said reactants at a temperature of from about 100° to about 400° F. to effect an alkylation reaction, a result of which is deactivation of said catalyst, said alkylation and catalyst reactivation being the principal reactions of the process;
   g. simultaneously withdrawing a second product stream from a fourth point located between said zone I and the next successive zone in the direction of flow (zone II); and,
   g. periodically advancing downstream the points of charging said reactants and said reactivation stream, and the points of withdrawal of said product streams to the next successive point for introducing inlet stream or withdrawing an outlet stream.

2. The process of claim 1 further characterized in that each of said zones contains 1 to 20 equivalent sub-beds of catalyst in series, each sub-bed having a fluid flow connecting path to connect said sub-bed with the previous and successive sub-bed in the series, and there being a point provided between each two sub-beds for introducing an inlet stream or withdrawing a product stream.

3. The process of claim 1 further characterized in that the points of charging said reactants and said reactivation stream and the points of withdrawing said product streams are periodically advanced downstream a substantially equal distance.

4. The process of claim 1 wherein at least a portion of said second product is recycled and admixed with said reactants stream.

5. The process of claim 1 wherein said reactants and reactivation streams are liquid streams and said reactivation stream includes no more than a saturation quantity of hydrogen.

6. The process of claim 1 wherein said Group VIII metal hydrogenation agent is selected from nickel, platinum, palladium, rhodium, and ruthenium.

7. A continuous fixed bed catalytic alkylation reaction and catalyst reactivation process comprising the steps of:
   a. providing a crystalline aluminosilicate zeolite catalyst composited with a Group VIII metal hydrogenation agent in a fixed bed containing three zones and having a fluid flow connecting path between said zones to interconnect said zones;
   b. arranging said zone in a series and providing fluid flow connecting means between the last zone and the first zone of the series to provide a directional circular flow path through said zones;
   c. providing a point between each two successive zones for introducing an inlet stream or withdrawing a product stream;
   d. introducing a reactivation stream including alkylatable hydrocarbon and hydrogen at a first point located between two successive zones to effect catalyst reactivation and to provide alkylatable hydrocarbon as a continuous component throughout said fixed bed of catalyst;

e. simultaneously withdrawing a first product stream from a second point located between another two successive zones;

f. simultaneously introducing reactants consisting essentially of isobutane or isopentane or a mixture thereof and at least one $C_2$-$C_5$ olefin into said fixed bed of catalyst at a third point located between the remaining two successive zones and reacting said reactants at a temperature of from about 100° to about 400° F. to effect an alkylation reaction, a result of which is deactivation of said catalyst, said alkylation and catalyst reactivation being the principal reactions of the process; and g. periodically advancing downstream the points of charging said reactants and said reactivation stream, and the point of withdrawal of said product stream to the next successive points for introducing an inlet stream or withdrawing an outlet stream.

8. The process of claim 7 further characterized in that each of said zones contains 1 to 20 equivalent sub-beds of catalyst in series, each sub-bed having a fluid flow connecting path to connect said sub-bed with the previous and successive sub-bed in the series, and there being a point provided between each two sub-beds for introducing an inlet stream or withdrawing an outlet stream.

9. The process of claim 7 further characterized in that the points of charging said reactants stream and said reactivation stream and the point of withdrawing said product are periodically advanced downstream a substantially equal distance.

10. The process of claim 7 further characterized in that said three points are located in successive order in a downstream direction as follows: first point, second point, and third point; and because of the cyclic nature of the process, said third point is followed by said first point.

11. The process of claim 7 further characterized in that said three points are located in successive order in a downstream direction as follows: first point, third point, and second point; and because of the cyclic nature of the process, said second point is followed by said first point.

12. The process of claim 7 wherein a portion of said product is recycled and admixed with said reactants stream.

13. The process of claim 7 wherein said reactant and reactivation streams are liquid streams and said reactivation stream includes no more than a saturation quantity of hydrogen.

14. The process of claim 7 wherein said Group VIII metal hydrogenation agent is selected from nickel, platinum, palladium, rhodium, and ruthenium.

* * * * *